United States Patent [19]

Salerno

[11] Patent Number: 4,940,462
[45] Date of Patent: Jul. 10, 1990

[54] SANITARY NAPKIN WITH EXPANDABLE FLAPS

[75] Inventor: Catherine E. Salerno, Millington, N.J.

[73] Assignee: McNeil-PPC, Inc., Milltown, N.J.

[21] Appl. No.: 160,739

[22] Filed: Feb. 26, 1988

[51] Int. Cl.$^5$ .............................................. A61F 13/16
[52] U.S. Cl. ................................... 604/387; 604/385.2
[58] Field of Search .................. 604/385.1, 385.2, 386, 604/397, 398, 387

[56] References Cited

U.S. PATENT DOCUMENTS

| 3,397,697 | 8/1968 | Rickard | 604/370 |
| 4,285,343 | 8/1981 | McNair | 604/387 |
| 4,579,556 | 4/1986 | McFarland | 604/385.2 |
| 4,589,876 | 5/1986 | Van Tilburg | 604/385.1 |
| 4,608,047 | 8/1986 | Mattingly | 604/387 |
| 4,687,478 | 8/1987 | Vantilburg | 604/387 |
| 4,690,679 | 9/1987 | Mattingly et al. | 604/383 |
| 4,692,163 | 9/1987 | Widlund et al. | 604/385.2 |
| 4,701,177 | 11/1987 | Ellis et al. | 604/385.2 |

FOREIGN PATENT DOCUMENTS

| 0249924 | 12/1987 | European Pat. Off. | 604/386 |
| 0301491 | 2/1989 | European Pat. Off. | 604/386 |

Primary Examiner—C. Fred Rosenbaum
Assistant Examiner—Mark O. Polutta
Attorney, Agent, or Firm—Andrea L. Colby

[57] ABSTRACT

Sanitary napkins are disclosed which include at least one flap having a portion that may be expanded longitudinally for permitting the flap to expand when folded over a side of an undergarment. This enables the flap to fold outwardly to the back of the undergarment and conform to the contour along the curved line of the crotch. Thus, an improved sanitary product is provided that provides side-protection along the entire longitudinal edges of the napkin.

7 Claims, 3 Drawing Sheets

SANITARY NAPKIN WITH EXPANDABLE FLAPS

CROSS REFERENCE TO RELATED APPLICATIONS

This application is related to co-pending application filed concurrently in the name of Pramod Mavinkurve, Ser. No. 160,966 filed Feb. 26, 1988, now allowed entitled "Sanitary Napkin Having an Elasticized Component", which is assigned to the assignee of this application and which is hereby incorporated by reference.

FIELD OF THE INVENTION

This invention relates to protective, absorbent liners for undergarments and more particularly, to providing more leak resistance for sanitary napkins having folding side panels or wings.

BACKGROUND OF THE INVENTION

Many of today's sanitary napkins are equipped with "side-protecting" flaps, or wings, that extend laterally from the longitudinal sides of a central absorbent. See Mattingly, U.S. Pat. No. 4,608,047, McNair, U.S. Pat. No. 4,285,343 and Van Tilburg, U.S. Pat. No. 4,589,876. These napkins typically function by having their users bend the lateral flaps downward along straight parallel hinge lines. Unfortunately, however, the crotch portion of most undergarments is concavely contoured to conform to the legs of the wearer. Thus, in order to accommodate a comfortable fit, only a portion of the side of the napkin has side protection. Accordingly, a need exists for a sanitary napkin that offers sanitary protection substantially along the entire longitudinal length of the napkin without substantially deforming the undergarment.

SUMMARY OF THE INVENTION

A sanitary napkin and method for applying a sanitary napkin are provided by this invention. The napkin includes flaps made of a stretchable, flexible material. These flaps can be, but are not necessarily limited to, extensions of the cover and backing of the absorbent element, and are also referred herein as "flap portions" of the napkin. The flaps and/or flap portions are designed to fold smoothly over the exterior of the panty and then to expand to conform with the contour of the undergarment. Adequate expandability can be achieved if the material used to effect this feature can elongate at least 110%, preferably about 150% of its prestretched length.

Thusly, the design flaw of the prior art, that only the center portion of the napkin offers the side protection of wings, can be overcome. This invention further provides for the contouring of the flaps of a sanitary napkin along the curved line of the crotch. If the flaps of a prior art napkin were extended from the transverse ends at the top end and the bottom of the central absorbent, the flap would be too wide at the center portion of the crotch resulting in "bunching" of the panty and attendant discomfort. The flaps of this invention, on the other hand, are expandable and can readily adapt to the contour of the panty without bunching. Additionally, the longitudinally extending sides of the absorbent element, which can comprise extensions of the impervious and pervious surfaces of the absorbent element, can be concavely configured and extended laterally to more appropriately conform to the contour of the panty crotch.

Accordingly, the long felt need of providing sanitary protection substantially along the entire longitudinal edges of sanitary napkins is provided. The flaps of this invention can be made expandable by using an elastic type element, by slitting an extension of the cover or barrier, or both, or by using an accordion or pleated flap material.

It is therefore an object of this invention to provide a sanitary napkin that more completely follows the contour of the undergarment it is attached to.

It is another object of this invention to provide a method of attaching a sanitary napkin so as to provide substantially complete lateral protection without bunching of the undergarment.

It is still another object of this invention to provide a sanitary napkin which can be folded smoothly around the crotch portion of a panty in comfortable fashion.

With these and other objects in view, which will become apparent to one skilled in the art as the description proceeds, this invention resides in the novel construction, combination, arrangement of parts and methods substantially as hereinafter described and more particularly defined in the attached claims.

BRIEF DESCRIPTION OF THE DRAWINGS

The accompanying drawings illustrate a complete embodiment of the invention according to the best mode for the best practical application of the principles thereof, and in which.

DESCRIPTION OF THE INVENTION

Figure 1:
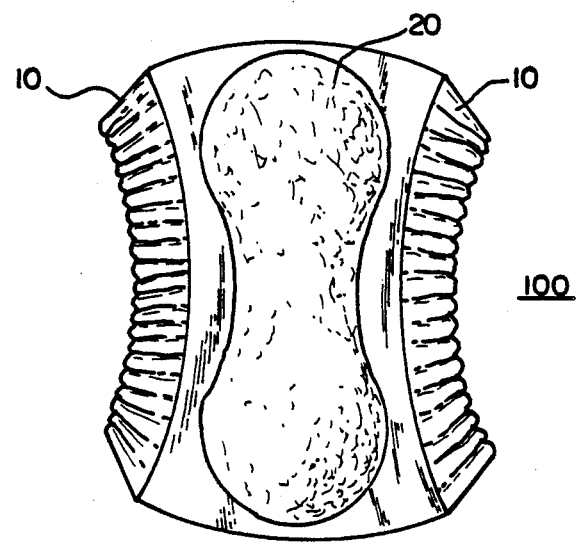
FIG. 1: is a planar view of the body-facing side of a sanitary napkin embodiment of this invention illustrating flexible flap portions extending along the longitudinal sides of the napkin.
Figure 2:
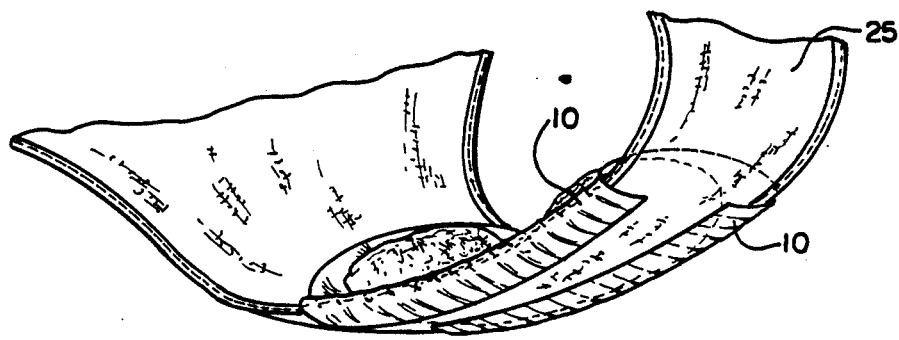
FIG. 2: is a perspective view of the application of the sanitary napkin embodiment of FIG. 1, illustrating how the flexible flap portions are folded around the crotch portion of the undergarment.

With reference to the drawings, and particularly FIGS. 1 and 2 thereof, there is shown a preferred sanitary napkin 100 having an absorbent element 20 having longitudinally extending sides, transverse ends, a body-facing side and an undergarment facing side. The flaps of this embodiment 10 to extend laterally from each of the longitudinal sides of the absorbent element and at least one of these flaps comprises a longitudinally extending resilient portion for permitting this flap to expand longitudinally when folded over a side of a crotch portion of an undergarment 25.

Figure 3:
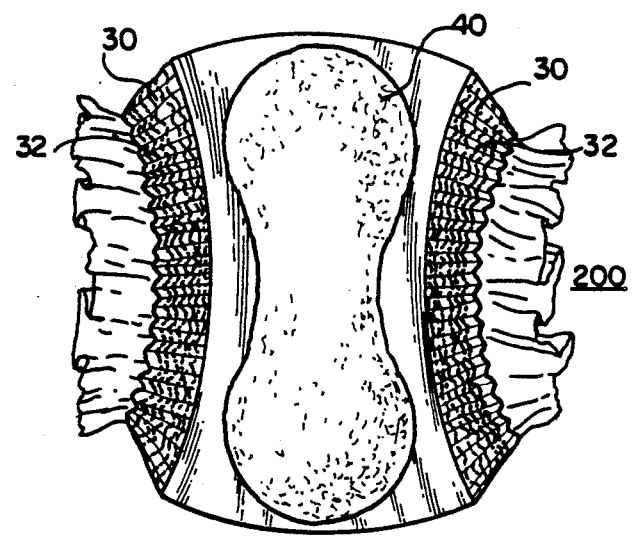
FIG. 3: is a planar view of the body-facing side of another sanitary napkin embodiment of this invention illustrating elastic stretch elements disposed within the flexible flap portions.
Figure 5:
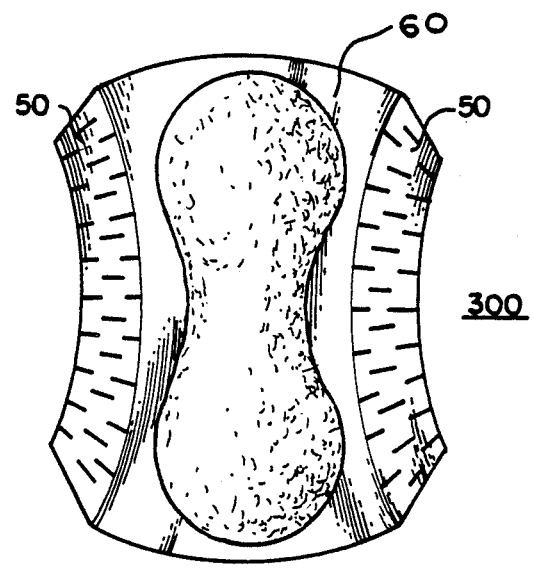
FIG. 5: is a planar view of the body-facing side of another sanitary napkin embodiment of this invention illustrating flexible flap portions containing slits for enabling these portions to expand.

As described by the embodiments of FIGS. 1, 3, 5, both of the flaps of the napkins of this invention can comprise longitudinally resilient flap portions 10, 30, and 50, which are ideally disposed substantially along the entire longitudinal sides of the napkins 100, 200, and 300. As illustrated, the flaps and/or resilient portions thereof 10, 30, 50 can comprise concave configured portions of the outwardly extending sides of the napkins 100, 200, and 300.

In order to accomplish the preferred "fit" of this invention, the flaps of these napkins 100, 200, and 300, preferably comprise stretchable material, including but not limited to elastic, perforated thermoplastic and pleated materials. If a thermoplastic material is selected for the flexible flap portion, it can comprise an extended portion of the body-facing side or undergarment-facing side of the absorbent element 20, 40, or 60. In each of the selected embodiments, the flaps should be expandable to about 110% to 200%, preferably about 130% to 175%, and most preferably to about 150% of their original or unstretched length. As used herein the "length" of the flaps refers to a flap measurement taken substantially parallel with the longitudinal sides of the absorbent element 20, 40, or 60.

Figure 4:
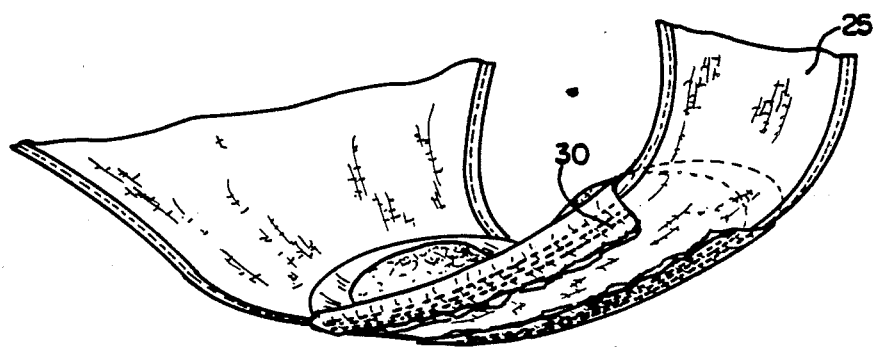
FIG. 4: is a perspective view illustrating the application of the sanitary napkin embodiment of FIG. 3 and further illustrating how the elastic elements are stretched.
Figure 6:
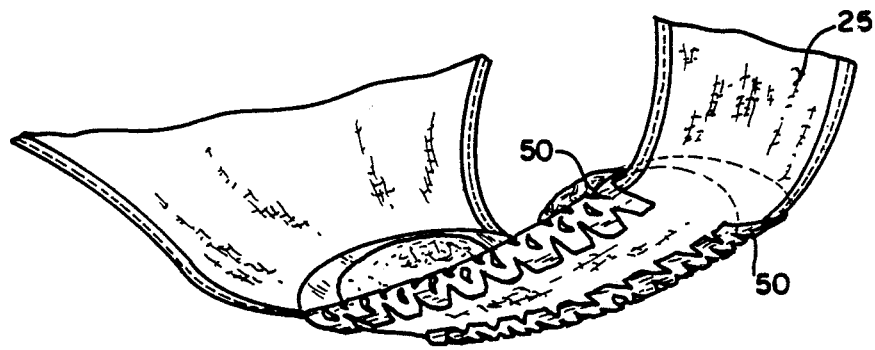
FIG. 6: is a perspective view of the application of the sanitary napkin of FIG. 5 illustrating how the flexible flap portions, including their slits, can be expanded to fold around the outer crotch portion of an undergarment.

Referring now to FIGS. 2, 4 and 6, the napkins 110, 200 of this invention can be novelly applied to the undergarment 25 by disposing their undergarment facing side onto the undergarment 25, and then folding the flaps over the sides of the crotch portion of the undergarment 25. In the preferred methods of this invention, the flaps are folded to substantially protect the entire longitudinal sides of the absorbent elements 20, 40 and 60.

In the preferred constructions, the absorbent elements 20, 40 and 60 can contain conventional resilient material for enabling the napkins 100, 200, and 300 to bend easily without excessive distortion. Such materials include compacted cellulosic fibers and hydrocolloidal material such as those described by Kopolow, U.S. Pat. No. 4,551,142, which is herein incorporated by reference. The preferred absorbent elements 20, 40, and 60 can be approximately –12 inches long, preferably about 8–11 inches. They generally comprise a core, which preferably is made of loosely associated absorbent hydrophilic materials such as cellulose fibers, wood pulp, regenerated cellulose or cotton fibers, and/or other materials generally known in the art. The absorbent element 20, 40 or 60 may be either rectangular or shaped.

As is customary in the art, covering the body-facing side of these napkins 100, 200 and 300 are body-fluid pervious surfaces. These body fluid pervious surfaces can be made of a resilient, relatively non-absorbing fluid pervious material. This material is provided for comfort and conformability and directs fluid to an underlying layer, for example wood pulp, which retains such fluid. These surfaces may be woven, or non-woven material pervious to body fluid. Furthermore, they should retain little or no fluid in their structure to provide a relatively dry surface next to the skin. Generally, the fluid permeable surfaces are a single, rectangular sheet of material having a width sufficient to cover the body-facing side of the absorbent elements 20, 40 and 60. Preferably, the fluid pervious surfaces are longer than the core so as to form end tabs, which may be sealed with other pervious or non-pervious layers to fully enclose the cores. The fluid pervious surfaces are preferably made of fibers or filaments of thermoplastic polymers such as polyethylene or polypropylene or apertured polymeric film.

Underlying the core of the absorbent elements 20, 40, and 60 can be another layer of absorbent material to provide additional resiliency to the product. This layer can extend beyond the longitudinal sides of the absorbent core to entrap any body fluid which escapes from the sides of the absorbent elements 20, 40 and 60. This layer may also be substantially wider than the core of the absorbent elements 20, 40 and 60 and may extend into the flaps. The absorbent layer may comprise a thin, absorbent layer of material such as tissue, fabric, or the like, made of cellulosic fibers. Because such material is provided as a safety measure and is only required to contain escaped fluid, it need not be very absorbent at all, and, in fact, may be comprised of any capillary or cellular system including hydrophobic material. However, the preferred material is a hydrophilic fabric comprised of cellulosic fibers such as wood pulp tissue or other suitable hydrophilic woven or non-woven material. The preferred tissue has the advantage of providing resiliency and conformability to the product.

The sanitary napkins 100, 200, and 300 of this invention further can include body-fluid impervious surfaces on their undergarment-facing sides. The impervious surfaces will preferably allow the passage of air and moisture vapor while blocking the passage of fluid to the outer surface. The impervious surfaces may be heat sealed or fastened by way of adhesives to a core or to a core wrapped in a pervious surface cover. The impervious surfaces may comprise any thin, flexible, body fluid impermeable material such as, a polymeric film, for example, polyethylene, polypropylene, cellophane or even a normally fluid pervious material that has been treated to be impervious, such as impregnated fluid repellent paper or non-woven fabric material. In the most preferred embodiments of this invention, the impervious surfaces include a plastic film of polyethylene or a bi-component film such as an EVA/PE coextruded film.

The preferred expandable flaps 20, 30, and 50 of this invention should be made of a stretchable, flexible material. The stretchability can be obtained by an elastic-type element 32, such as that described in FIG. 3. Similarly the requisite stretchability may be obtained by providing slits or perforations, as described in FIGS. 5 and 6, in an extension of the cover and/or barrier of the absorbent element 60. Alternatively, this flexibility can be incorporated into the napkins by using a polymeric foam, i.e. polyurethane foam, or an accordion-pleated flap material, such as that described in FIGS. 1 and 2. The percent elongation required depends upon the width of the flaps employed, and generally the flexible flaps 10. 30 and 50 should accommodate an elongation of about 110–200, preferably about 125–175%, and most preferably about 150% of their original length.

Although preferably not including absorbent pulp materials, the flaps 10, 30, and 50 of this invention can also include a body fluid impervious backing such as the materials described in connection with the above-mentioned body-fluid impervious surfaces. It is also expected that the flaps 10, 30 and 50 can comprise body fluid Pervious covers, much like the above-mentioned body-fluid pervious layers, and absorbent tissues disposed between their covers and their backings. In addition, it is preferred that the flaps 10, 30, and 50 of this invention contain absorbent tissue with sufficient capillary action to retain small quantities of escaped liquid. This tissue can be heat sealed or adhesively sealed around the edges of the flaps 10, 30, and 50 with the preferred impervious backings and body fluid pervious covers of the flaps 10, 30, and 50 to form absorbent areas.

Also included with this invention are attachment adhesives which can be made of any known, pressure-sensitive adhesive material. As used herein, the term "pressure-sensitive" refers to any releasable adhesive or releasable tenacious means. Adhesive compositions suitable for sanitary napkins, include, for example, the water-based, pressure-sensitive adhesives such as acrylate adhesives. Alternatively, the adhesive may comprise rapid setting thermoplastic "hot-melt", rubber adhesives, or two- sided adhesive tape. As is customary in the art, a preferred kraft paper release strip can also be applied to these adhesive compositions to protect them prior to use.

From the foregoing it can be realized that this invention Provides improved side-protection for winged sanitary napkins. Although various embodiments have been illustrated, this was for the purpose of describing, but not limiting, the invention. Various modifications, which will become apparent to one skilled in the art, are within the scope of this invention described in the attached claims.

I claim:
1. A sanitary napkin comprising
   (a) an absorbent element having longitudinally extending sides, transverse ends, a body-facing side and an undergarment facing side;
   (b) stretchable, longitudinally resilient flaps extending outwardly along said longitudinally extending sides, said flaps expanding longitudinally when folded over a side of a crotch portion of an undergarment.
2. The sanitary napkin of claim 1 wherein said flaps are disposed substantially along the entire longitudinally extending sides of said napkin.
3. The sanitary napkin of claim 2 wherein said flaps comprise outwardly extending concave sides.
4. The sanitary napkin of claim 3 wherein said flaps are expandable to 110% to 200% of their original length.
5. The sanitary napkin of claim 3 wherein said flaps are expandable to 130% to 175% of their original length.
6. The sanitary napkin of claim 3 wherein said flaps are expandable to about 150% of their original length.
7. A sanitary napkin comprising:
   (a) an absorbent element having longitudinally extending sides, transverse ends, a body-facing side, and an undergarment facing side; and
   (b) flaps extending laterally from and substantially along the entire length of each of said longitudinal sides of said absorbent element, said flaps having longitudinally expandable portions therein, whereby said flaps can be expanded to fold over a crotch portion of an undergarment to provide sanitary protection substantially along said entire length of each of said longitudinal sides.

* * * * *

(12) EX PARTE REEXAMINATION CERTIFICATE (5242nd)
United States Patent
Salerno

(10) Number: US 4,940,462 C1
(45) Certificate Issued: Dec. 6, 2005

(54) SANITARY NAPKIN WITH EXPANDABLE FLAPS

(75) Inventor: Catherine E. Salerno, Millington, NJ (US)

(73) Assignee: McNeil-PPC, Inc., Milltown, NJ (US)

Reexamination Request:
No. 90/003,684, Dec. 30, 1994
No. 90/003,996, Oct. 12, 1995

Reexamination Certificate for:
Patent No.: 4,940,462
Issued: Jul. 10, 1990
Appl. No.: 07/160,739
Filed: Feb. 26, 1988

(51) Int. Cl.$^7$ ............................................. A61F 13/16
(52) U.S. Cl. .................................. 604/387; 604/385.04

(56) References Cited

U.S. PATENT DOCUMENTS

| | | |
|---|---|---|
| 4,166,464 A | 9/1979 | Korpman ................... 128/287 |
| 4,589,876 A | 5/1986 | Van Tilburg |
| 4,608,047 A | 8/1986 | Mattingly |
| 4,692,163 A | 9/1987 | Widlund ...................... 604/385 |
| 4,891,258 A | 1/1990 | Fahrenkrug ................. 428/138 |
| 5,267,992 A | 12/1993 | Van Tilburg ................ 604/387 |

FOREIGN PATENT DOCUMENTS

| | | |
|---|---|---|
| JP | 4036391 | 12/1965 |
| JP | 2168253 A | 6/1986 |

*Primary Examiner*—Tatyana Zalukaeva

(57) ABSTRACT

Sanitary napkins are disclosed which include at least one flap having a portion that may be expanded longitudinally for permitting the flap to expand when folded over a side of an undergarment. This enables the flap to fold outwardly to the back of the undergarment and conform to the contour along the curved line of the crotch. Thus, an improved sanitary product is provided that provides side-protection along the entire longitudinal edges of the napkin.

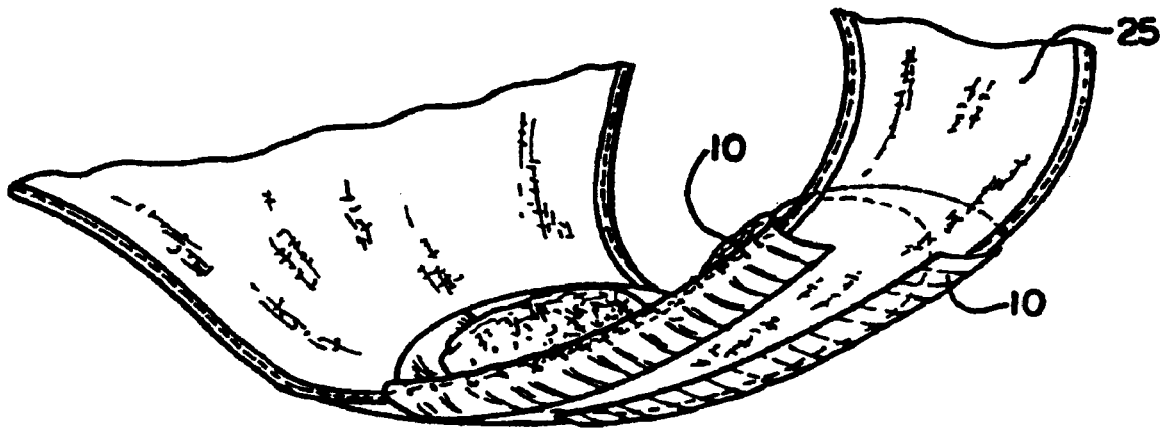

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–7 are cancelled.

* * * * *